US006735530B1

(12) United States Patent
Guarnieri

(10) Patent No.: US 6,735,530 B1
(45) Date of Patent: May 11, 2004

(54) COMPUTATIONAL PROTEIN PROBING TO IDENTIFY BINDING SITES

(75) Inventor: Frank Guarnieri, Brooklyn, NY (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/183,267

(22) Filed: Oct. 30, 1998

Related U.S. Application Data

(60) Provisional application No. 60/101,521, filed on Sep. 23, 1998.

(51) Int. Cl.$^7$ ........................... G06F 17/00; G06F 17/30

(52) U.S. Cl. ........................................ 702/27; 702/19

(58) Field of Search .............................. 702/19, 27, 22; 530/350; 435/7.1, 6

(56) References Cited

FOREIGN PATENT DOCUMENTS

| EP | 0 807 687 A2 | 11/1997 |
| WO | WO 96/34347 | 10/1996 |
| WO | WO 97/16177 | 5/1997 |

OTHER PUBLICATIONS

Guarnieri et al. J.Amer. Chem. Society, 118, 8493–8494, 1996.*
Lee, Probing the Abilities of Synthetically Useful Serine Proteases to Discriminate between the Configurations of Remote Stereocenters Using Chiral Aldehyde Inhibitors(Journal of the American Chemical Society, 1996, 118/3, 502–508).*
Lunazzi, Conformational Studies by Dynamic NMR, 58.1 Stereodynamics of C–C and C–N Rotation in Furan and Thiophene o–Amino Thioaldehydes and Aldehydes (Journal of Organic Chemistry, 1997, 62/7 (2263–2266).*
Clough, Molecular Dynamics Simulation of Substituted Conjugated Ionic Polyacetylenes (Macromolecules, Feb. 15, 1993, vol. 26, No. 4, pp. 597–600).*
Raineri; Surrogate Hamilitonian description of solvation dynamics. Resolution of global responses into spatial profiles. (Chemical Physics 183 (1994), pp 187–205.*
Siepmann; Monte Carlo study of the properties of self–assembled monolayers formed by adsorption of CH3(CH2)15 SH on the (111) surface of gold.; Molecular Physics, 1993, vol. 79, NO 3, pp 457–473.*
Morgantini; Solvation Free Energies of Amides and Amines: Disagreement between Free Energy Calculations and Experiment; J. Am. Chem. Soc. 1995, 117, pp 6057–6063.*
Calafat; A New Arrangement for the Anticancer Antibiotics Tallysomyein and Bleomycin When Bound to Zinc: An Assessment of Metal and Ligand Chirality by NMR and Molecular Dynamics; J. Am. Chem. Soc 1997. pp 119, 3656–3664.*

Blasko; Pendant–Capped Porphyrins. 2. Structural Analysis and Dynamics of the Biphenyl Pendant–Capped Porphyrin Model of Catalase . . . (J.A. Chem. 1993, 58, pp 5738–5747).*
Koone, Diffusion of Simple Liquids in Porous Sol–Gel Glass, (Journal of Physical Chemistry, Nov. 16, 1995, vol. 99, No. 46, pp 16976–16981).*
Gibson, Crystal Packing without Symmetry Constraints. 2. Possible Crystal Packings of Benzene Obtained by Energy Minimization from Multiple Starts, (Journal of Physical Chemistry, Mar. 16, 1995, vol. 99, No. 11, pp 3765–3773).*
Brandmeier, 8. Antiparellel B–Sheet Conformation in Cyclopeptides Containing a Pseudo–amino Acid with Biphenyl Moiety, (Helv. Chim. Acta, 1994, 77(1) pp 70–85).*
Parks, Resonance Ionization Spectroscopy 1990, (Institute of Physics Conference Series No. 114).*
Basson, NMR of montan wax, (J. Phys. D: Appl. Phys. 1998, 21(9), pp 1434–7).*
Mokrosz, Conformational Analysis of 4-(2–Furyl)–2–(methylamino) pyrimidine. (Journal of Heterocyclic Chemistry, Jul./Aug. 1996, vol. 33, Nol. 4. pp. 1207–1210).*
Duggan, H and C Nmr Relaxation Studies of Molecular Dynamics of the Thyroid Hormones Thyroxine 3, 5, 3,'–Triiodothyronine, and 3,5–Diiodothyronine, (Journal of Medicinal Chemistry, Sep. 27, 1996, vol. 3, No. 20, pp 4007–4016).*
Dennis, S., et al., "Computational mapping identifies the binding sites of organic solvents on proteins," *Proc. Natl. Acad. Sci. USA* 99:4290–4295, National Academy of Sciences (Apr. 2002).

(List continued on next page.)

*Primary Examiner*—Michael Borin
(74) *Attorney, Agent, or Firm*—Sterne, Kessler, Goldstein, Fox P.L.L.C.

(57) ABSTRACT

Provided is a computer-implemented method of analyzing a macromolecule for potential binding sites that includes: positioning an instance of a computer representation of a molecule or molecular fragment at a plurality of sampling sites of the macromolecule; selecting a value of B, wherein $B=\mu'/kT+\ln<N>$, where $\mu'$ is the excess chemical potential, k is Boltzmann's constant, T is the absolute temperature, and <N> is the mean number of molecules of the molecule or molecular fragment; repositioning the instances of the molecule or molecular fragment; accepting or rejecting each instance of the repositioned molecule or molecular fragment based on the Metropolis sampling criteria using the computed binding energy compared to the selected value of B; repeating these steps at a lesser value of B; outputting a list of unrejected instances of the molecule or molecular fragment, wherein the molecule or molecular fragment is an organic fragment; and outputting a list of one or more clusters of sampling sites, wherein the clusters of sampling sites include closely located or superimposed sampling sites associated with the unrejected instances of the molecule or molecular fragment.

10 Claims, 16 Drawing Sheets

OTHER PUBLICATIONS

Ding, X., et al., "Nature of the Inactivation of Elastase by N–Peptidyl–O–aroyl hydroxylamine as a Function of pH," *Biochemistry 34*:7749–7756, American Chemical Society (1995).

Honma, T., "Recent Advances in De Novo Design Strategy for Practical Lead Identification," *Med. Res. Rev. 23*:606–632, Wiley (Sep. 2003).

Johnson, P.M., "Resonance ionization spectra as a reflection of excited state dynamics," *Inst. Phys. Conf. Ser. No 114: Section 4*:145–150, IOP Publishing Ltd. (1991).

Kortemme, T., and Baker, D., "A simple physical model for binding energy hot spots in protein–protein complexes," *Proc. Natl. Acad. Sci. USA 99*:14116–14121, National Academy of Sciences (Oct. 2002).

Massova, I., and Kollman, P.A., "Computational Alanine Scanning to Probe Protein–Protein Interactions: A Novel Approach To Evaluate Binding Free Energies," *J. Am. Chem. Soc. 121*:8133–8143, American Chemical Society (Published in Print: Sep. 1999, Published on Web: Aug. 31, 1999).

Mattos, C., et al., "Analogous inhibitors of elastase do not always bind analogously," *Struct. Biol. 1*:55–58, Nature Publishing Co. (1994).

Mattos, C., et al., "Structural Analysis of the Active Site of Porcine Pancreatic Elastase Based on the X–ray Crystal Structures of Complexes with Trifluoroacetyl–Dipeptide–Anilide Inhibitors," *Biochemistry 34*:3193–3203, American Chemical Society (1995).

International Search Report for International Application No. PCT/US03/07366, Sarnoff Corporation, filed Mar. 11, 2003, International Searching Authority/US, Alexandria, Virginia, (mailed Oct. 30, 2003).

Calafat, A.M., et al., "A New Arrangement for the Anticancer Antibiotics Tallysomycin and Bleomycin When Bound to Zinc: An Assessment of Metal and Ligand Chirality by NMR and Molecular Dynamics," *J. Am. Chem. Soc. 119*:3656–3664, American Chemical Society (Apr. 1997).

Guarnieri and Mezei, Simulated Annealing of Chemical Potential: A General Procedure for Locating Bound Waters. Application to the Study of the Differential Hydration Propensities of the Major and Minor Grooves of DNA, *J. Am. Chem. Soc., 118, 8493–8494* (1996).

H. Resat et al., Use of the Grand Canonical Ensemble in Potential of Mean Force Calculations, *J. Phys. Chem., 100*, 1426–1433 (1996).

H. Resat and M. Mezei, Grand Canonical Ensemble Monte Carlo Simulation of the dCpG/Proflavine Crystal Hydrate, *Biophysical Journal, vol. 71*, 1179–1190 (1996).

Lynch and Pettitt, Grand canonical ensemble molecular dynamics simulations: Reformulation of extended system dynamics approaches, *J. Chem. Phys, 107*, 8594–8610.

Chan et al., Core Structure of gp41 from the HIV Envelope Glycoprotein, *Cell, vol. 89*, 263–271 (1997).

Edwards and Bernstein, Synthetic Inhibitors of Elastase, *Medicinal Research Reviews, vol. 14, No. 2*, 127–194 (1994).

* cited by examiner

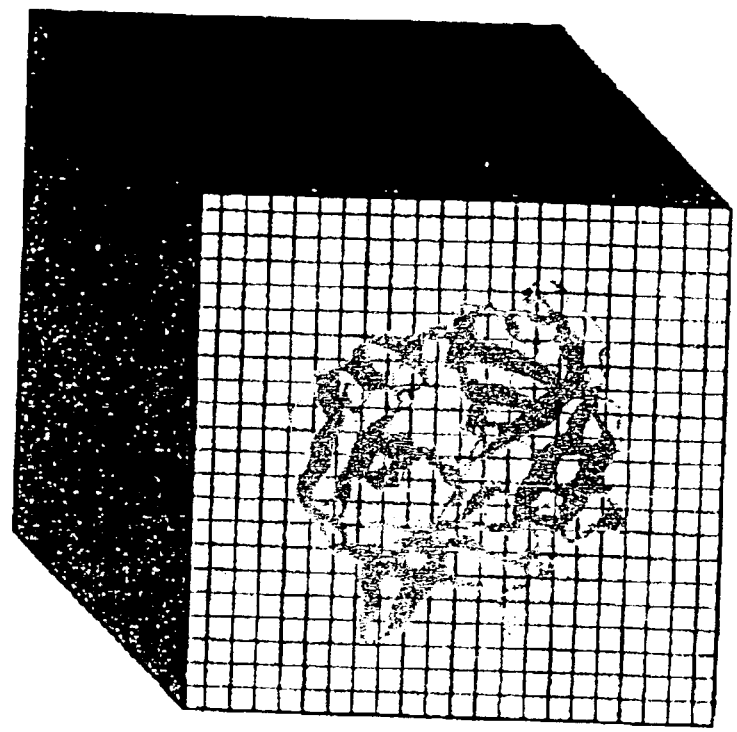
FIG. 1B
FIG. 1A

COMPUTATIONAL PROTEIN PROBING TO IDENTIFY BINDING SITES

The present application claims the priority of US Provisional Application No. 60/101,521, filed Sep. 23, 1998.

The present invention relates to methods of identifying binding sites on proteins, methods for identifying classes of compounds suitable for binding a protein, and methods of conducting experiments to identify compounds that interact with a protein to affect a biological process.

Determinations of protein structures have to date been conducted by isolating crystals of the protein of interest, and analyzing structure by X-ray crystallography. Typically, the protein has been co-crystallized with heavy metal component, or subjected to multiple co-crystallizations, with the heavy metal providing a reference for solving the crystallographic data.

With a determination of the structure of a protein, or the structure of another macromolecule having significant tertiary structure, such as a DNA or RNA, workers often seek to identify the binding sites that are or may be of significance to a biological process, such as an enzyme active site or a site for interacting with another macromolecule or with itself. Computational efforts have been focused on efforts to sample the surface of a molecule to find good fits with known binding agents. These methods have had modest success, and are dependent on knowledge of (a) the structure of good binding agents and, often, (b) the function of the protein. A more traditional approach has sought to co-crystallize binding substances with the macromolecule to identify binding sites. With the binding site identified, educated guesses can be made as to new molecules that could bind the site. These educated guesses can guide synthetic methods, including combinatorial chemistry methods, to make and test new molecules. When such prospective binding agents prove effective binding agents, and possibly are also found effective in an appropriate biological model, the structural correlations drawn from the results can be tied to information about the binding site to make still further inferences about the structure important to a biological function. This co-crystallization approach depends on an initial knowledge of active agents, and is experimentally difficult and time consuming.

The present inventor has found a method of identifying, from a three-dimensional structural solution of a macromolecule, the binding sites for molecules. The structural solution used as the basis for the method can be derived from crystallography, spectroscopic analyses such as NMR, computational derivations, or any other method of determining the structure of a macromolecule. The method does not require or typically use information on the function of the macromolecule, as the method avoids subjective biases and instead depends purely on physical parameters. Further, the method can be refined further to narrow the possible choices of binding sites and identify the functionalities, i.e., organic fragments or "ORFs," that effectively interact with the binding site(s). The data obtained for ORFs further identifies the orientations of the functionalities useful in a candidate binding agent, thereby providing a tool for searching chemical databases to identify candidate binding agents. Where the methods described herein identify more than one potential binding site, the data generated through these methods can be used to energetically rank the binding sites, and thereby quantitatively determine which site has the potential to more strongly bind molecules.

The computational method described here generates maps of binding site preferences that are nearly identical with maps produced by compiling data generated by traditional methods, but with one important difference—the experimentally produced data took many years to produce while the data produced as described herein can be produced in no more than a few weeks. The invention provides an important development in unbiased simulation methods for predicting the character of agents that bind to biological macromolecules to affect the function of the macromolecules.

SUMMARY OF THE INVENTION

In one embodiment, provided is a method of identifying binding sites on a macromolecule comprising: (a) for at least one organic fragment (ORF), conducting, at separate values of parameter B, two or more simulated annealing of chemical potential calculations using the ORF as the inserted solvent; and (b) comparing converged solutions from step (a) to identify first locations at which the relevant ORF is strongly bound, thereby identifying candidate sites for binding ligand molecules. In one preferred aspect, the method further comprises: (c) identifying clusters of sites that strongly bind an ORF. In another preferred aspect, the method further comprises: (d) conducting steps (a) and (b) for each of two or more ORFs and identifying clusters where two or more distinct ORFs bind. Preferably, a cluster that binds three or more distinct ORFs is identified. The method can identify further functionalities that contribute to the binding of bioactive agents by reducing the binding stringency in the vicinity of a cluster to further identify elements that would contribute to the binding of a bioactive agent.

In another preferred aspect, the method further comprises: (e) conducting, at separate values a measure of chemical potential, two or more simulated annealing of chemical potential calculations using water as the inserted solvent; (f) comparing converged solutions from step (c) to identify locations at which water is strongly bound, thereby identifying locations on the protein which are not candidate sites for binding ligand molecules; and (g) identifying first locations that are not water locations.

In still another preferred aspect, the simulated annealing of chemical potential calculations comprise multiple steps of sampling, and wherein in a number of steps of the sampling the ORFs position is changed by a small amount and the resulting new position is accepted or rejected based on the change in energy as a result of the change attempted.

Further provided is a method of identifying the chemical characteristics of compounds that bind a macromolecule comprising examining the functionalities and relative orientations of the ORFs found in a cluster pursuant to the binding site identifying method outlined above.

Also provided is a method of conducting combinatorial chemistry to identify compounds that interact with a macromolecule comprising: (a) identifying classes of reactants that are modeled by the functionalities of the ORFs found in a cluster pursuant to the binding site identifying method of macromolecule; (b) designing a combinatorial synthetic protocol that calls for two or more synthetic procedures that react reagents of at least two of the classes identified in step (a); and (c) conducting the combinatorial synthetic protocol to create candidate binding molecules.

Further provided is a method of conducting a bioactive agent discovery process comprising: (a) from a group of established combinatorial synthetic protocols or a collections of chemical compounds or pools of chemical compounds, identifying those members of the group that provide a high density of compounds that meet for a macromolecule selection criteria identified from the binding site identifying method of macromolecule; and (b) conducting binding or functional assays to identify compounds obtained from the identified collections or protocols which bind or affect the function of the macromolecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates a solved crystal structure, while FIG. 1B displays the structure with a grid is imposed.

Figure 3A:
FIGS. 3A and 3B show the combined results for several ORFs bound to elastase after simulations at relatively low B values, with the results in FIG. 3B filtered to identify clusters of these bound ORFs.
Figure 3B:
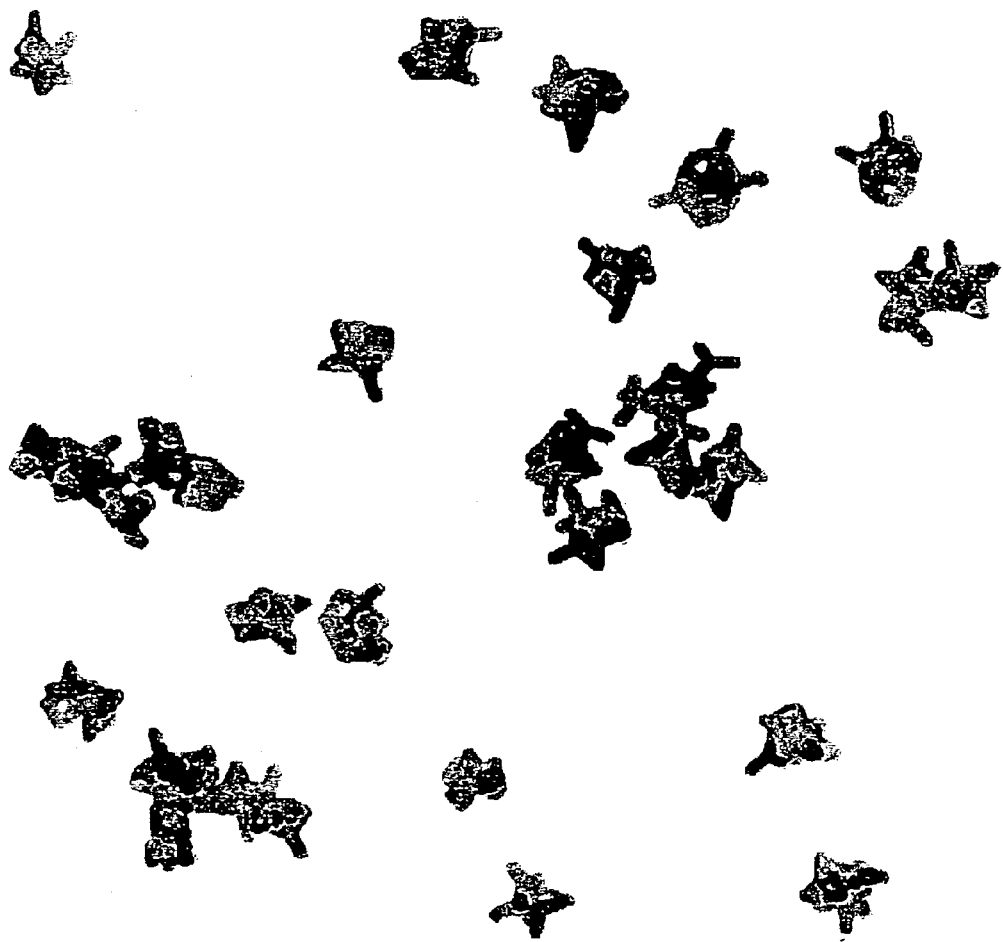
Figure 3C:
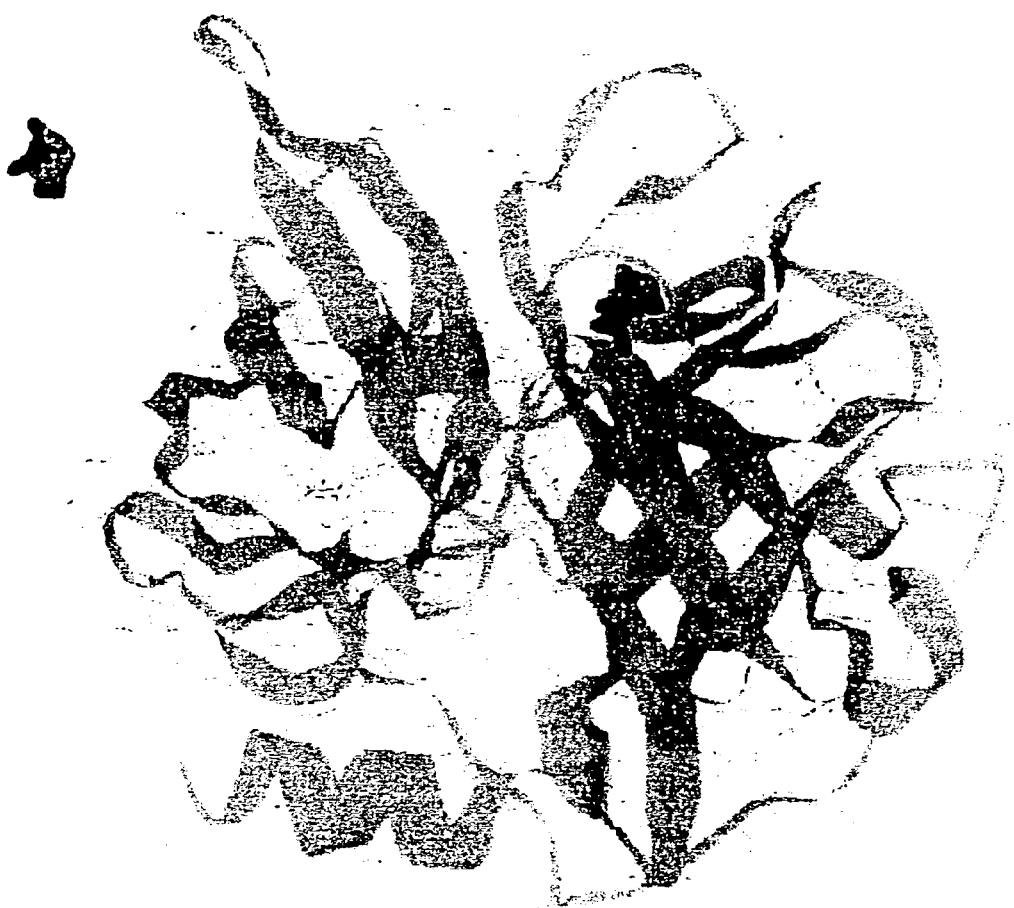
FIG. 3C shows the two clusters of FIG. 3B which remain after excluding strong water binding sites.
Figure 3D:
FIG. 3D shows the one cluster that remains after extending the analysis to another ORF.
Figure 3E:
FIG. 3E shows the analysis extended to still a further ORF.
Figure 3F:

The panels of FIG. 3F compare the simulation results to a co-crystallography result.

Figure 4B:
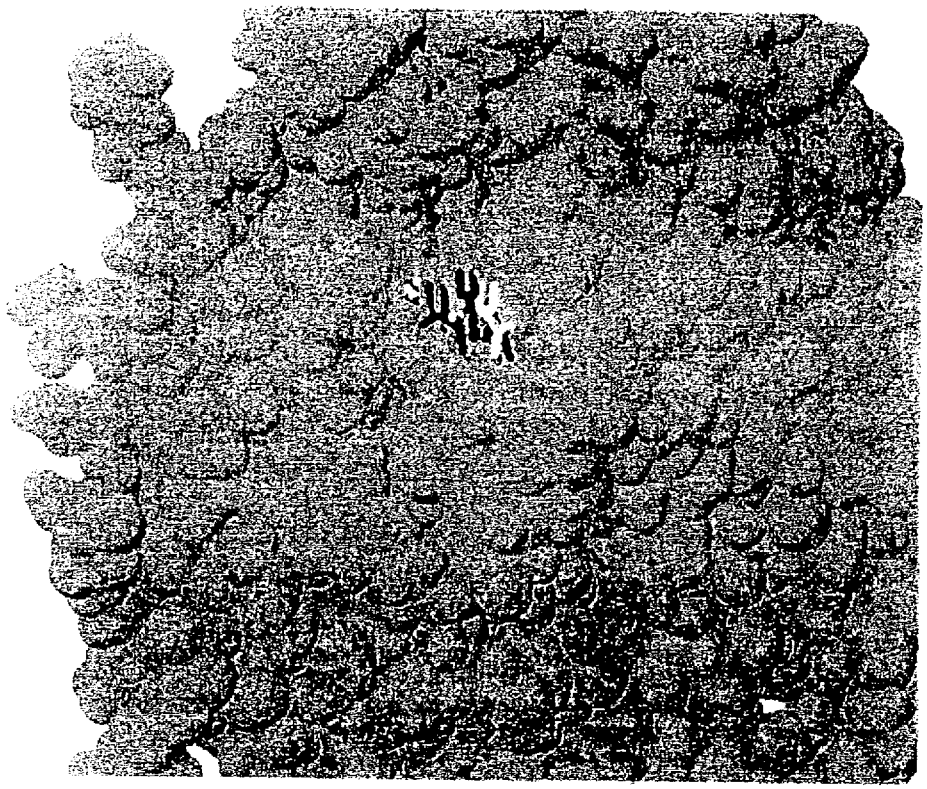
Figure 4A:
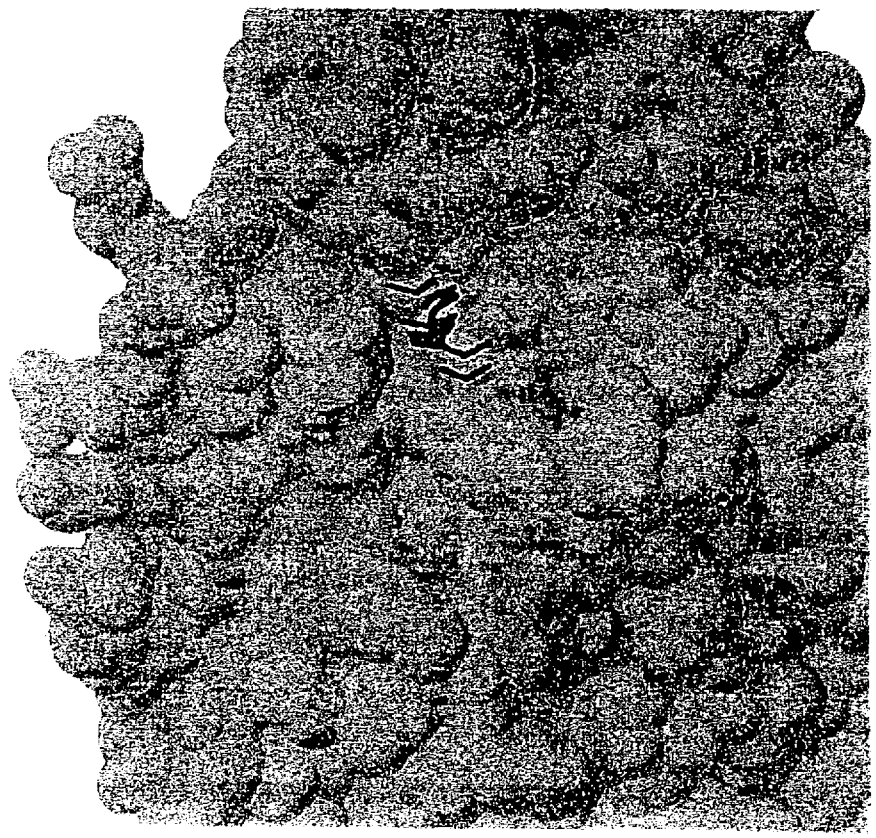

Illustrated in FIG. 4A are the amide binding sites extracted from the data of six co-crystallization experiments with elastase and known ligands; and illustrated in FIG. 4B is a cluster of the highest affinity amide binding sites determined by the simulation method of the invention.

Figure 4C:

Illustrated in FIG. 4C are the amide ORFs of FIG. 4B plus amides which are in the vicinity of the cluster but which appear in the simulation at second highest affinity binding values.

Figure 5B:
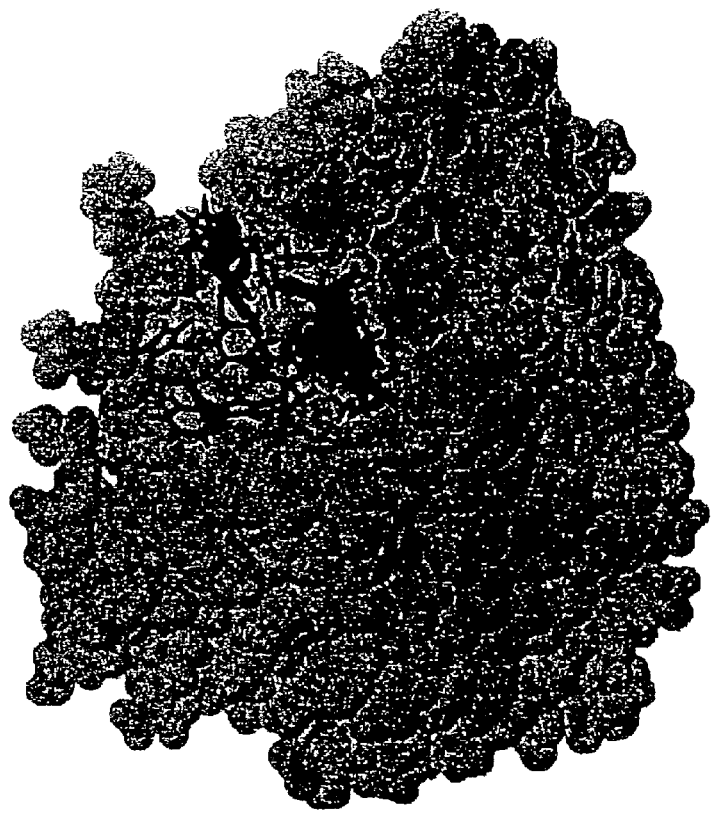
Figure 5A:
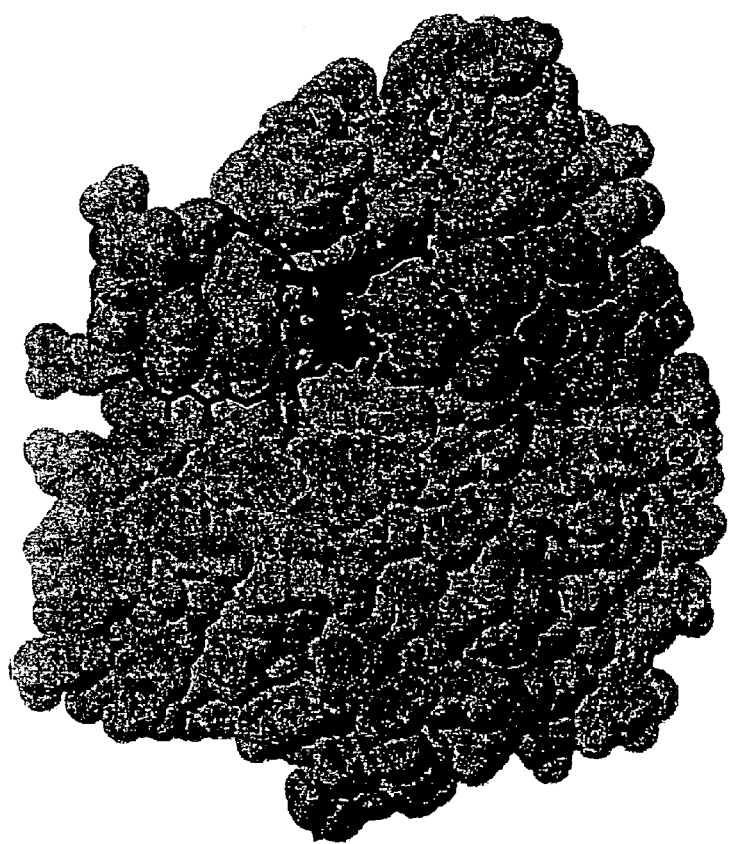

In FIGS. 5A and 5B, solutions obtained with co-crystals of elastase inhibitors are compared with data obtained by the methods herein described.

Figure 6B:
Figure 6A:

FIGS. 6A and 6B show the surfaces of elastase involved in binding ligands as indicated by the crystallographic data, FIG. 6A, and as indicated by the solutions obtained the method described herein, FIG. 6B.

Figure 7:
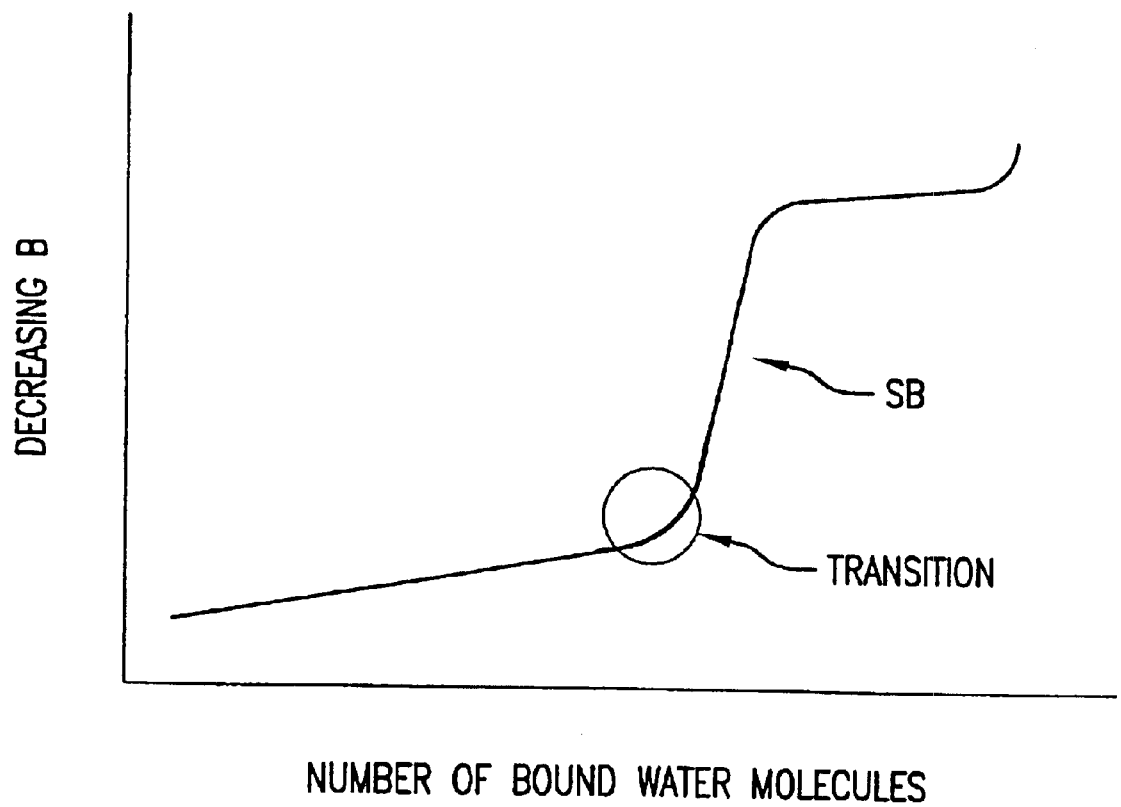

FIG. 7 shows a schematic illustration of the type of titrations for water binding to a macromolecule that can be used to help identify a level of relatively strong water binding.

GLOSSARY

The following terms shall have, for the purposes of this application, the respective meaning set forth below.

"Boactive agent" refers to a substance such as a chemical that can act on a cell, virus, organ or organism, including but not limited to drugs (i.e. pharmaceuticals) to create a change in the functioning of the cell, virus, organ or organism. In a preferred embodiment of the invention, the method of identifying bioactive agents of the invention is applied to organic molecules having molecular weight of about 600 or less or to polymeric species such as peptides, proteins, nucleic acids, proteoglycans and the like. A bioactive agent can be a medicament, i.e. a substance used in therapy of an animal, preferably a human.

"Cluster of free grid points" refers to free grid points that are within a "cluster" in that, relative to a given ORF, there is a sufficient number of nearby or adjacent free grid points to allow a reasonable probability that the ORF could be inserted at the cluster. Thus, the cluster of free grid points for $H_2O$ must be defined to identify all volumes at the surface or interior of a macromolecule that could accommodate $H_2O$—though the selection criteria should err to identifying some volumes that do not accommodate $H_2O$, as needed to assure that all appropriate volumes are sampled in the simulation process. A cluster of free grid points is defined differently depending on the size of the ORFs (e.g., compare $H_2O$ and benzene) and the spacing of the grid.

A "cluster of ORF binding sites" typically refers to a pattern of closely located or superimposed sites that bind ORFs with sufficient affinity to merit further consideration.

"Collection of chemical compounds" refers to any collection of compounds collected or organized with the intention that they can be examined to identify bioactive agents (e.g., having a biological activity measured directly or through a surrogate for biological activity such as binding to a macromolecule or interfering with a function of a macromolecule). The collection can be prepared from a collection of simpler molecules (which can be bound to a support) by a chemical scheme designed to generate a diversity of chemicals. Collections of this latter type are often referred to as "combinatorial libraries."

"Free grid points" refers to grid points (which are discussed below) which are, for a given accepted definition of atomic radius, "free" in that they do not fall within the atomic radii of the mapped atoms of the relevant macromolecule.

"Macromolecule" refers to a molecule or collection of molecules which has a time-averaged tertiary structure. Thus, while the term typically refers to proteins, ribonucleic acids, structures formed of both nucleic acid and protein, carbohydrates, structures formed of two or more of the aforementioned, and the like, it can also refer to structures formed with other molecules including lipids. Macromolecules are used in the method described herein with reference to maps of their tertiary structure. Such maps are typically generated by X-ray diffraction studies, which have generated maps for thousands of macromolecules. However, maps can be produced by other methods such as computational methods or computational methods supplemented by other data such as NMR data. While computational methods have been difficult to apply, recent studies appear to have achieved some successes.

Organic fragments or "ORFs are molecules or molecular fragments that can be used to model one or more modes of interaction with a macromolecule, such as the interactions of carbonyls, hydroxyls, amides, hydrocarbons, and the like.

Water locations are locations at which water is strongly bound, meaning, in one embodiment, for example locations where the simulation indicates water remains bound when the simulation is run at values of B that are equal to or less than the B value for the transition point indicating those water molecules that are strongly influenced by the macromolecule. Illustrated in FIG. 7 is a conceptualization of the titration of simulated bound water molecules with decreasing values of B, a parameter described further below. A transition point indicates water molecules that are strongly influenced by the macromolecule. A B value less than or equal to that at the transition point can be designated as defining water binding of sufficient strength to render competitive binding by another molecule unlikely, as illustrated by point SB in the illustration. Typically, for a water soluble protein, this point SB is selected so that about 100 to about 50 water molecules remain bound for a 50 kd protein.

DETAILED DESCRIPTION OF THE INVENTION

The simulation process of the present invention works by artificially inserting a given ORF at an unbiased sampling of all the sites on or within a macromolecule structure where such ORF can, as a practical matter, reside. These sites can be termed the "sampling sites." Typically, a schedule of simulations for each of a number of ORFs are run, with each simulation run at a separate value of a parameter B, which is related to the excess chemical potential. The schedule provides for simulations conducted at each of a number of B values, typically ranging from to about −15. In each simulation at a given value of B, the simulation assesses at each step of the simulation whether the insertion of the ORF at a given site shall be accepted or rejected, with the assessment based on a grand canonical ensemble probability density function. At each step of the simulation, the algorithm models the insertion of the ORF at the site. A forced bias canonical probability density function is used to translate and rotate the ORF in small steps (e.g., ±0.2 Å, ±30°) to identify an energy minimized insertion given the simulation parameters in place at the time of the simulation step. The probability of the insertion is then determined from the grand canonical ensemble probability density function, and the ORF can be represented as resident at the site by a random number generating protocol weighed to the probability value. Alternative methods for choosing to make this representation, such as applying cutoff values for when to represent the insertion or not, can also be applied, but are less favored. Typically, following a successful insertion, the subsequent deletion attempts at the site are with the previously identified translated and rotated ORF, and this translated and rotated ORF is used until a deletion attempt succeeds. The simulation is typically conducted for a large number of steps, such as $2\times10^6$ steps, with the majority of the steps, e.g., $1.5\times10^6$ required to "equilibrate" the simulation so that the number of accepted insertions is equal to the number of deletions on average.

By taking a large number of unbiased samplings at each sample site over the latter course of the simulation, such as after every 200 steps of iterations after equilibrium is achieved, an occupation probability of the ORF residing at that sample site at the given value of B can be assessed. The occupancy as an overall result of the method can then be determined based on this probability, for example with a random number protocol making the representation based on its probability. The degree to which the ORF is translated or rotated can also be represented based on the probability of such translations and rotations.

For each ORF, simulations are run at each of a number of values of a measure of excess chemical potential, such as B. Thus, as this value lowers, the retention of an ORF at a given sampling site is an indication of high relative binding affinity.

The sampling sites are typically arrived at by creating a grid as illustrated in FIG. 1. FIG. 1 illustrates a solved crystal structure (FIG. 1A) on which a grid is imposed (FIG. 1B). For example, the grid can have about ½ Å to about 1 Å spacing, with the grid intersection points defining the candidates for sampling sites. The spacing of the grid is preferably selected to be less than the smallest cross-section of the ORF. The spacing is typically selected to be small enough in relation to the size of the ORF so that the probability that free volumes that could define free grid point clusters have sufficient free grid points to allow useful sampling as described below. Such relatively small spacing minimizes the chance that the selection of how to orient the grid will bias the algorithm against identifying certain ORF binding preferences. The sampling sites are selected from sites that are unoccupied by the macromolecule (FIG. 1B). A final elimination of "grid bias" is achieved by varying the test insertion points away from strict initial insertion at grid points, as described below.

The sampling sites are limited to those sites having enough adjacent volume free of the macromolecule to allow the ORF to be inserted. For example, the sampling sites can be limited to grid points within an open area of at least about 2 Å×2 Å×2 Å (=8 $Å^3$ or 0.008 $nm^3$) or about 2.5 Å×2.5 Å×2.5 Å (=15.6 $Å^3$ or 0.0156 $nm^3$) or, for water, about 2.2 Å×2.2 Å×2.8 Å. The grid points can be selected for those free grid points that are within a cluster of free grid points, such as, for example, a cluster of 3, 4, 5, 6, 7, 8 or more free grid points, depending on the size of the ORF and the spacings of the grid.

In one preferred embodiment, the ORF is not necessarily initially inserted exactly at the grid points, but instead at a random sampling of insertion points within a short distance of the grid points, such as points within a sphere shape centered at the grid point and having a diameter of about some percentage, such as 10%, of the grid spacing, or within a box shape centered at the grip point having width, length and height of about such a percentage of the grid distance. As discussed above, this "wobble" in the initial insertion point helps eliminate grid bias where the placement of the grid happens to reduce the chance that a given open volume will be efficiently sampled.

Figure 2A:
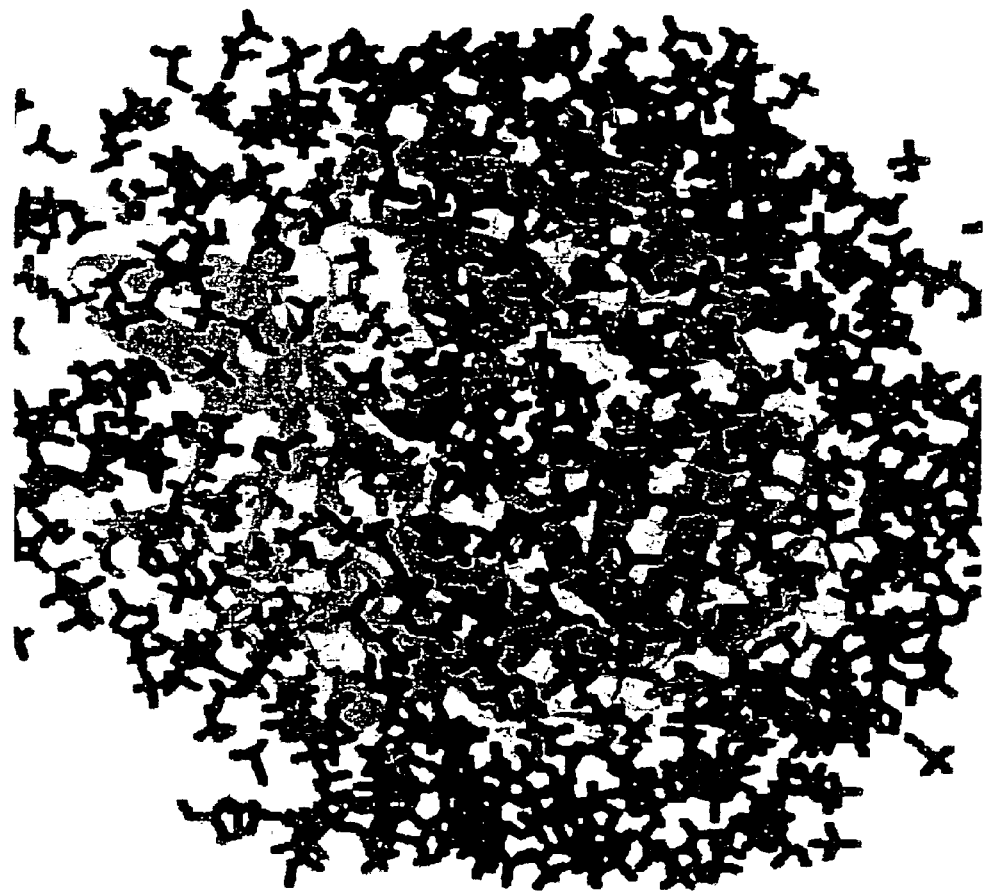
FIGS. 2A–2D display the method of the invention applied to the crystallographic solution of elastase, the method can be exemplified using methanol as the ORF.
Figure 2B:
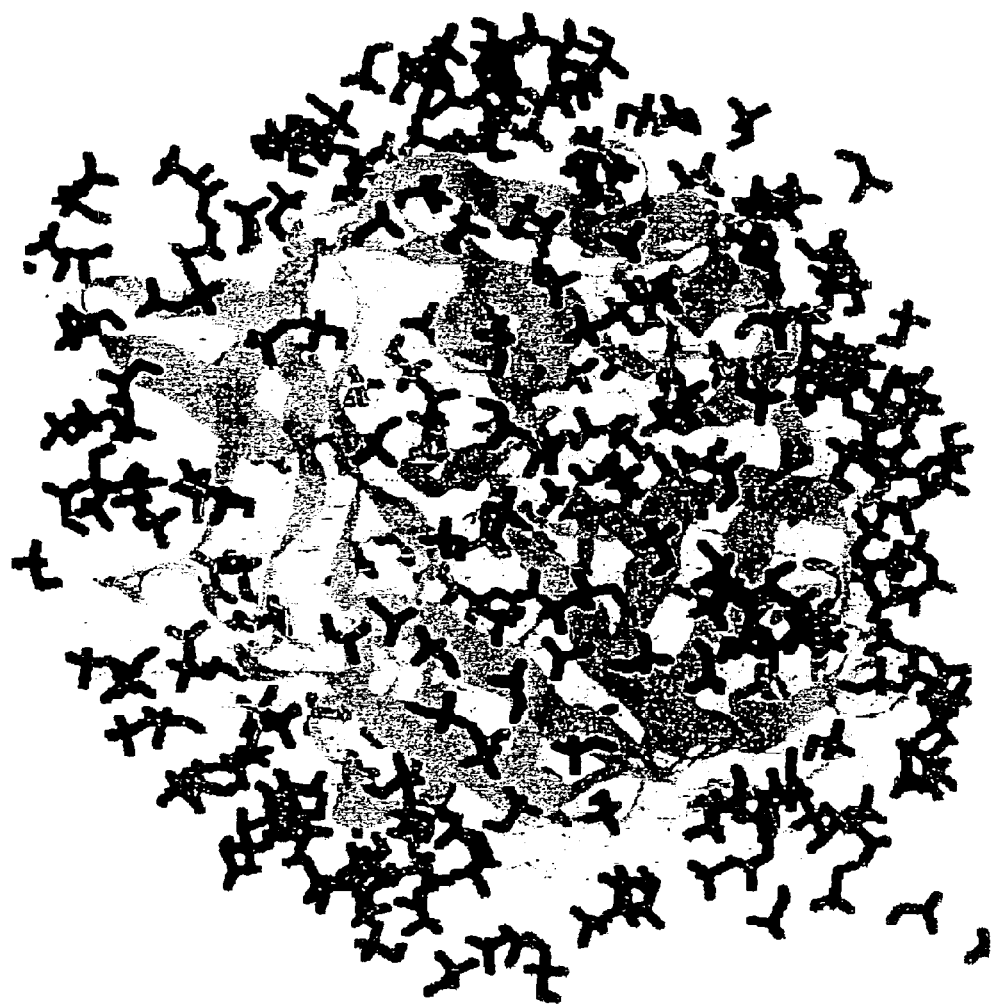
Figure 2C:
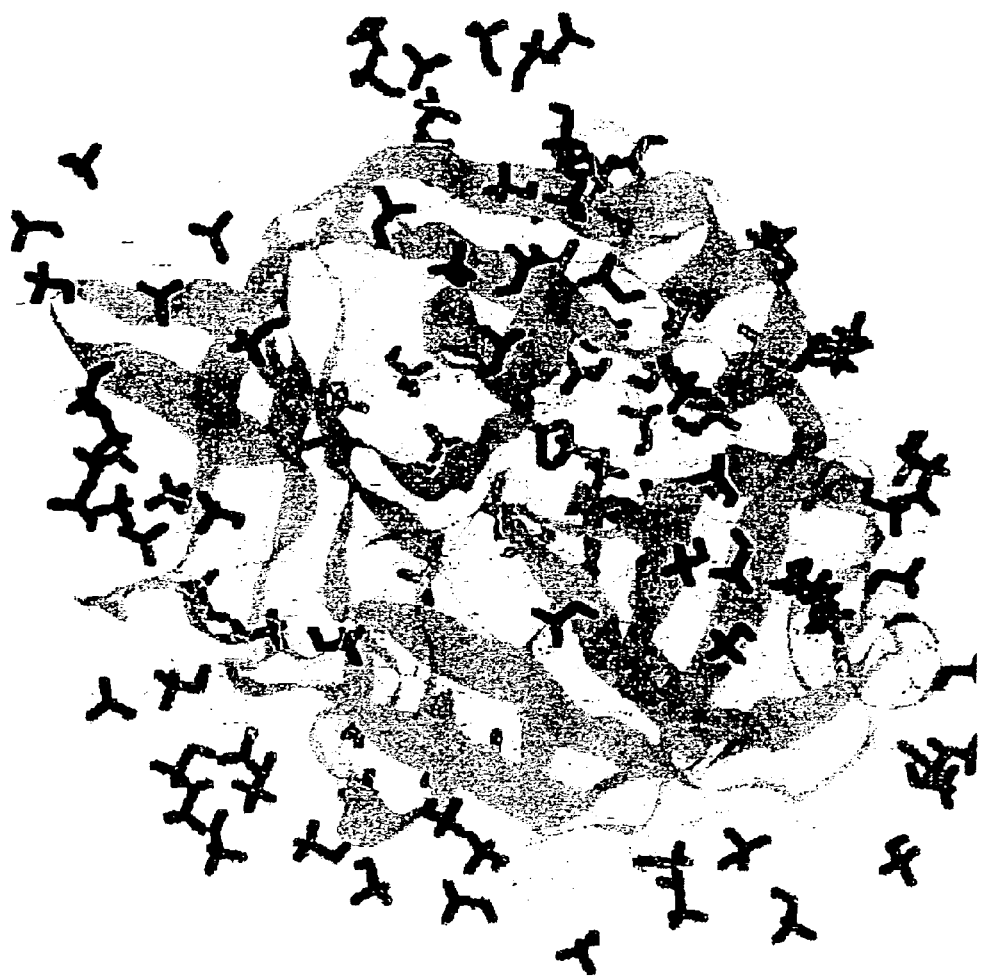
Figure 2D:
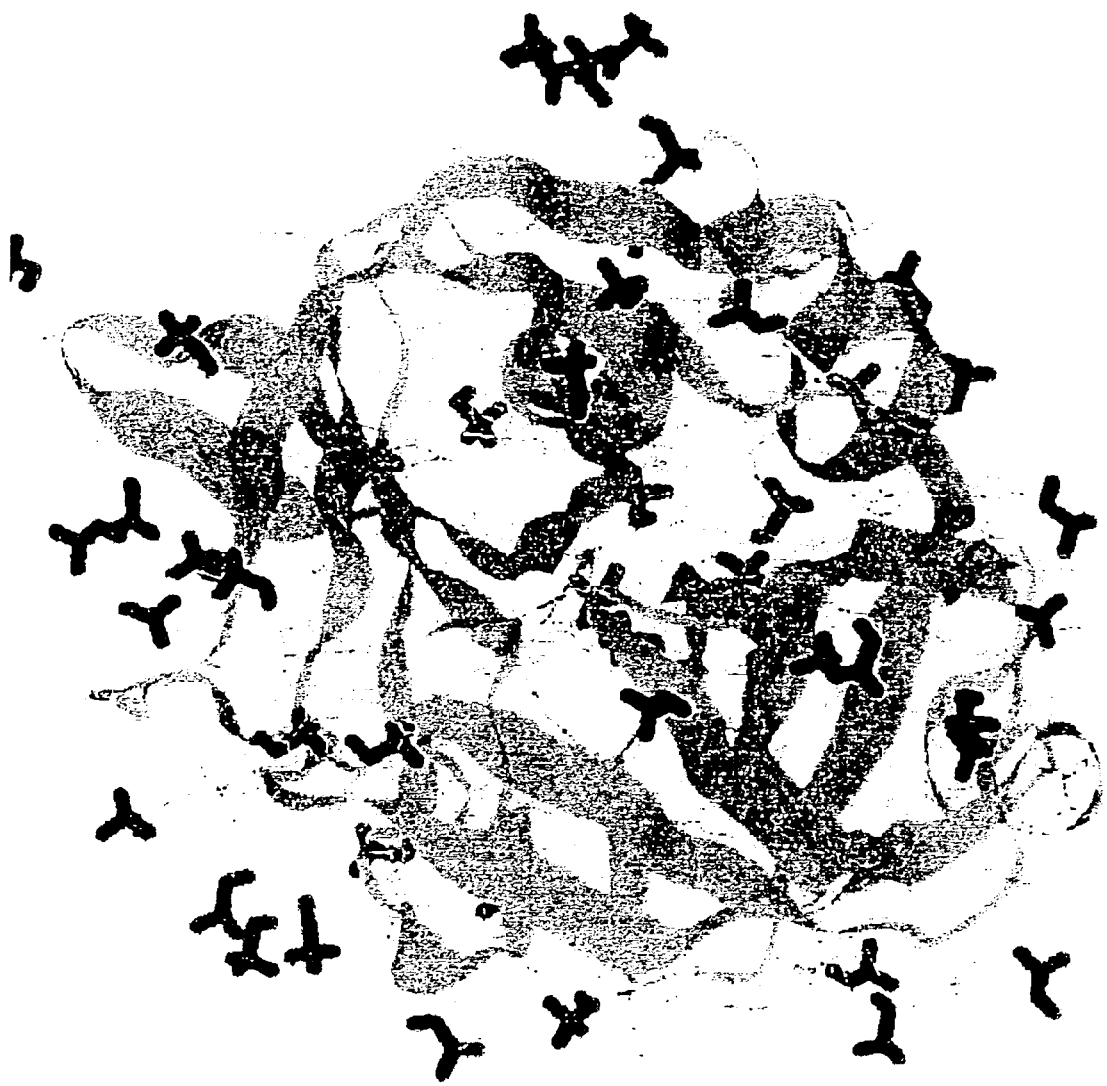

Using the crystallographic solution of elastase, in particular, the pig pancrease elastase structural solution of G.A. Petsko of Brandeis University, the method can be exemplified using methanol as the ORF. FIG. 2A shows the final solution using a relatively high B value, e.g., B=10. FIG. 2B shows the final solution using an intermediate value, e.g., B=6 or 7. FIG. 2C shows the final solution using a lower intermediate value, e.g., B=0 or −2 or 4. FIG. 2D shows the final solution using a restrictive value, such as B=−14. As illustrated, with lower values of B less and less methanol molecules remain bound. These remaining methanol fragments indicate those that bind with relatively high affinity.

The next step of the process is to conduct simulations with additional ORFs and identify clusters of relatively high affinity ORF binding sites. Thus, for example, again using elastase, simulations can be conducted to determine binding for ORFs for ammonia, methanol, ketone and amide. Combined results at relatively low B values are illustrated in FIG. 3A. Clusters of ORF binding sites are identified in FIG. 3B. The method of the present invention seeks to identify clusters of ORF binding sites, where the clusters can be made up solely of one type of ORF. Preferably, however, the cluster will include binding sites for 2, 3, 4, 5, 6, 7 or more distinct ORFs.

Examples of useful ORFs include:

| Name | Structure |
| --- | --- |
| Acetone | $CH_3(C=O)CH_3$ |
| Aldehyde | $H(C=O)—CH_3$ |
| Amide | $H(C=O)NH_2$ |
| Ammonia | $NH_3$ |

-continued

| Name | Structure |
|---|---|
| Benzene | (benzene ring) |
| Carboxylic Acid | $CH_3COOH$ |
| 1,4-Diazine | (pyrazine ring) |
| Ester | $CH_3-O-(C=O)-CH_3$ |
| Ether | $CH_3-O-CH_3$ |
| Formaldehyde | $H_2C=O$ |
| Furan | (furan ring) |
| Imidazole | (imidazole ring) |
| Methane | $CH_4$ |
| Methanol | $CH_3OH$ |
| Phospho-Acid | $HO-P(=O)(OH)-OH$ |
| Pyridine | (pyridine ring) |
| Pyrimidine | (pyrimidine ring) |
| Pyrrole | (pyrrole ring) |
| Thiol | $CH_3SH$ |
| Thiophene | (thiophene ring) |

Preferably, the ORFs selected are representative of chemical features that have proven useful in the design of pharmaceuticals or other bioactive chemicals.

Thus, in a first mode of analysis, an important part of the process is to run the simulations with several ORFs, identifying clusters of sites that bind multiple ORFs with relatively high affinity. These clusters are strong candidate sites for ligand binding sites. Moreover, the relative positioning of the ORFs is instructive of the features of good binding agents. For example, at the binding site identified on elastase by the methods described below, a cluster having two benzene rings with an amide interposed between them models some of the strongest elastase inhibitors derived from an extensive research program, which inhibitors have a sulfonamide in place of the carbon-based amide of the simulation. See, Tables XXIII and XXV of Edwards et al., "Synthetic Inhibitors of Elastase," *Medicinal Research Reviews* 14:127–194, 1994.

In some implementations of the invention, clusters of ORF binding sites alone will identify, or substantially narrow the range of choices for, the sites at which ligands interact with a given protein. However, in some embodiments of the invention, the sites that bind water strongly are identified, and the clusters that intersect with strong water binding sites are discounted. Thus, in the elastase example, the candidate ligand binding sites of FIG. 3B are narrowed by excluding water binding sites, as illustrated in FIG. 3C. If the analysis is extended to five ORFs as illustrated in FIG. 3D, a single candidate site remains. FIG. 3E shows a slightly different perspective of the same site illustrated in FIG. 3D, with the analysis extended to six ORFs. FIG. 3F shows how well the candidate site (left panel) matches up with the structure of a co-crystal containing the ligand trifluoroacetyl-lysyl-prolyl-pisopropylanilide.

Accordingly, in a second mode of analysis, an optional step in the process is to narrow the choices for ligand binding sites by excluding ORF clusters that intersect with relatively strong water binding sites.

It should be noted that clusters of ORFs are typically identified at relatively low B values, thereby helping to identify prospective binding sites for ligands. However, further information about prospective binding sites can be gleaned by looking, in the vicinity of a prospective binding site, at more weakly binding ORFs. This information value flows from the prospect of more weakly binding ORFs modeling a ligand interaction which, while weak in isolation, models a real contribution to ligand binding affinity of a bioactive agent as a whole. Illustrated in FIG. 4A are the amide binding sites extracted from the data of six co-crystallization experiments with elastase and known ligands. Illustrated in FIG. 4B is a cluster of the highest affinity amide binding sites determined by simulation. Illustrated in FIG. 4C are the amide ORFs of FIG. 4B plus amides which are in the vicinity of the cluster but which appear in the simulation at the second highest affinity values. As illustrated, this last step of expanding the results by looking at neighboring lower affinity ORF binding sites helps to better model the results seen in co-crystallography. Specifically, the cluster results identify the site at which the majority of amide binding sites are seen in crystallography, but the expansion extends the results to another cleft in elastase where amides have been experimentally located. Additionally, the expansion identifies part of another cleft at which ligand interactions are seen (as will be illustrated in other Figures).

Thus, in a third mode of analysis, the features of ligand binding sites indicated by other modes of analysis are expanded upon by looking to less stringent simulation results in the vicinity of ORF clusters. The above illustration focused on a cluster of one type of ORF, but is applicable with clusters of many types of ORFs, where the expansions can be limited to one type of ORF or multiple types of ORFs.

The data in FIGS. 4A–4C illustrate an important concept. Both in actual ligand bindings and in the simulations, multiple effective binding locations and orientations for a given type of moiety can be found to overlap. This reflects the existence of multiple local energy minima. In real world actions, rather than low temperature averaging obtained by crystallography, binding interactions will reflect a range of such local minima.

In FIGS. 5A and 5B, solutions obtained with co-crystals of elastase inhibitors are compared with data obtained by the methods herein described. In FIG. 5A, the solutions for six co-crystallized inhibitors are shown, with the inhibitor molecules overlaid on each other (non-space-filling representation, with the elastase segment represented by a space-filling illustration). These inhibitors are trifluoroacetyl-1-lysyl-1-prolyl-p-isopropylanilide (Mattos, C. et al., *Nat. Struct. Biol.* 1:55–58(1994); crystal solution: PDB ID: 1ELA, trifluoroacetyl-1-lysyl-1-leucyl-p-isopropylanilide (Mattos, C. et al., *Nat. Struct. Biol.* 1:55–58 (1994); crystal solution: PDB ID: 1ELB, trifluoroacetyl-1-phenylalanyl-p-isopropylanilide (Mattos, C. et al., *Nat. Strict. Biol.* 1:55–58(1994); crystal solution: PDB ID: 1ELC, trifluoroacetyl-1-phenylalanyl-1-alanyl-p-trifluoromethylanilide (Mattos, C. et al., *Biochemistry* 34:3193–203(1995); crystal solution: PDB ID: 1ELD, trifluoroacetyl-1-valyl-1-alanyl-p-trifluoromethylanilide (Mattos, C. et al., *Biochemistry* 34:3193–203 (1995): crystal solution: PDB ID: 1ELE and n-tert-butoxycarbonyl-alanyl-alanyl)-o-(p-nitrobenzoyl) hydroxylamine (Ding, X. et al., *Biochemistry* 34:7749–56 (1995): crystal solution: PDB ID: 1ELF. In FIG. 5B, the solutions for approximately 10 ORFs, which are in their respective high affinity protein binding states are overlaid. Both methods identify a region which favors the binding of aromatic moieties. The simulation process achieves approximately 90% 3D geometric identity with the crystallography results.

FIGS. 6A and 6B show the regions of elastase involved in binding ligands as indicated by the crystallographic data, FIG. 6A, and as indicated by the solutions obtained from the computational method described herein, FIG. 6B.

The simulations of the invention utilize a Monte Carlo algorithm. The form of Monte Carlo simulation useful in the present invention is described in Frenkel and Smit, "Understanding Molecular Simulation: From Algorithms to Applications," Academic Press, New York, 1996. The simulation method can comprise:

Locate a numeric representation of the macromolecule in a periodic cell.

Optimize the position of the macromolecule in the cell.

Locate all the cavities in the macromolecule, whether interior or surface cavities.

Insert and delete the ORFs (including water) in these cavities.

Compute the probabilities of occupation of the ORFs using a grand canonical ensemble probability density function.

Vary the chemical potential yielding relative free energies of binding.

The methodology, grand-canonical ensemble simulation, can be introduced as follows:

Grand-Canonical Ensemble Simulations

The distinguishing feature of simulations in the grand-canonical ensemble is the change in the number of molecules (ORFs) in the system during the simulation. In other words, the sampling is not restricted to the configuration space of a given dimension but it has to be extended to a set of configuration spaces. Applicant has found, unexpectedly, that the complexity of allowing for these changing numbers of molecules and the resulting changing mass nonetheless makes the simulation computationally extremely more efficient. The change in the number of molecules corresponds to the fact that the grand-canonical partition function $\Xi$ is the linear combination of the corresponding canonical partition functions of a different number, N, of molecules, Q:

$$\Xi(T, V, \mu) = \sum_{N=}^{\infty} \frac{\exp(\mu N / kT)}{N!} Q(T, V, N) \quad (1)$$

where T is the absolute temperature, $\mu$ is the chemical potential, k is the Boltzmann constant, and Q(T,V,N) is defined by:

$$Q(T, V, N) = q^N \int \exp(-E(X^N)/kT) dX^N \quad (2)$$

with q being the molecular partition function.

The sampling of the configuration space of N molecules (ORFs) has been shown to be feasible using Metropolis Monte Carlo methods where in each step of the sampling a molecule's (ORFs) position is changed by a small amount and the resulting new conformation is accepted or rejected based on the change in energy, $\Delta E$, as a result of the change attempted. This position shifting can be thought of as effecting a "shaking" of the ORF to identify its favored positioning, and the "shaking" methodology, which can be biased in the direction of the forces can be termed "forced bias Monte Carlo." When this shaking is applied, the simulation solutions reflect higher probability orientations. Accordingly:

$$P_{move}^{acc} = \min(1, \exp(-\Delta E/kT)) \quad (3)$$

Notice that the temperature (kept constant during the simulation) enters the acceptance formula as a scaling factor of the energy change.

Generalizing the canonical ensemble Metropolis method to simulations in the grand-canonical ensemble calls for steps where the number of molecules (ORFs) changes. Operationally, this requires either the deletion of an existing molecule or the 'creation', i.e., insertion of a new one. It has been shown that when the deleted molecule is chosen randomly, then the deletion attempt should be accepted with the following probability:

$$P_{del}^{acc} = \min\left(1, \exp(-\Delta E/kT - B)\frac{N}{V}\right) \quad (4)$$

where $$B = \mu'/kT + 1N> \quad (5)$$

with $\mu'$ being the excess chemical potential, N the number of molecules (ORFs), <N> its Boltzmann average and V the volume of the system (which is a constant during the simulation). Attempts to insert a molecule (ORF) at a random location is accepted with the following probability:

$$P_{ins}^{acc} = \min\left(1, \exp(-\Delta E/kT + B)\frac{V}{N+1}\right) \quad (6)$$

Here the effect of the chemical potential is introduced into the acceptance expression via the B parameter. The presence of the factors V and N follows from the relation between the canonical and grand-canonical partition functions: when a molecule (ORF) is taken out of the system, the integration over its coordinates (in $Q_N$) will yield a V factor and N is the last factor of N!. They can also be given a probabilistic interpretation: the insertion site will be chosen with probability IIV and the molecule (ORF) to be deleted will be chosen with probability 1/N.

The simulation proceeds by alternating attempts to move, insert and delete molecules (ORFs) and accepting them with probabilities $P_{move}^{acc}$, $P_{ins}^{acc}$, $P_{del}^{acc}$ as defined by Equations (3–5) above. After sufficiently long runs, the number of molecules (ORFs) N will fluctuate around its Boltzmann average <N>. If a given density has to be simulated then it is generally necessary to try different B values. In this regard, it is useful to note the following relationship:

$$\left(\frac{\partial <N>}{\partial B}\right) T, V = <N^2> - <N>^2 \quad (7)$$

This method has been found useful in simulating atomic fluids at moderate densities but runs into difficulties when room-temperature liquids are simulated. The difficulty stems from the fact that most insertion attempts will be at positions where there already is a molecule (e.g., from the solved protein structure) resulting in a large $\Delta E$, and the resulting probable rejection of the attempt.

To increase the efficiency of insertion attempts, a cavity-biased insertion technique was introduced. Insertions are attempted only at sites where a cavity of suitable size already exists, thereby ensuring a non-negligible probability of acceptance. However, to ensure that the simulation thus modified still produces the required Boltzmann distribution, both the insertion and deletion acceptance probabilities have to be modified. The modified expression involves the probability of finding a cavity when there are N molecules (ORFs) present, $P_N^{cav}$, which follows from:

$$P_{ins}^{acc} = \min\left(1, \exp(-\Delta E/kT + B)\frac{P_N^{cav} N}{N+1}\right) \quad (8)$$

$$P_{del}^{acc} = \min\left(1, \exp(-\Delta E/kT - B)\frac{N}{P_N^{cav} V}\right) \quad (9)$$

In Equations 8 and 9, $P_N^{cav}$ N represents the volume of the regions of the system that contain cavities of suitable size. The efficiency of the cavity-biased method follows from the fact that the algorithm searching for cavities also yields $P_N^{cav}$ without extra steps. Calculations on a variety of fluids (water, benzene), which define ORFs, have confirmed that the cavity biased method significantly increases the efficiency of insertion attempts and allows modeling of densities that proved to be impractical without this improvement.

Water Binding

Aspects of the simulations used in the invention can be illustrated with calculations used to determine the strength of water binding to a synthetic polynucleotide (Guarnieri, F., and Mezei, M., J. Am. Chem. Soc. 118:8493–8494 (1996)). This illustration can be described as follows:

This text illustrates how the method of simulated annealing of chemical potential allows bulk waters to be distinguished from bound waters, and how differentially bound waters may be distinguished from each other based on their relative chemical potentials. This is illustrated by showing that it takes more free energy to desolvate the minor groove than the major groove of a charged DNA dodecamer.

Grand canonical ensemble simulations are generally performed by placing a molecule in a periodic simulation cell, setting a parameter B, which is representative of free energy, in such a way as to achieve an experimentally determined density, sampling potential hydration positions around the molecule by inserting and deleting water molecules from the simulation cell using a technique such as cavity-bias (Mezei, M., Mol. Phys. 61:565–582 (1994); Resat, H., and Mezei. M., J. Am. Chem. Soc. 116:7451–7452 (1994)), and accepting or rejecting the attempt based on a Metropolis Monte Carlo (Metropolis, N. et al., J. Chem. Phys. 21:1087–1092 (1953)) criteria using a grand canonical ensemble probability function (Tolman, R., in The Principles of Statistical Mechanics, Dover Press. New York (1971)). The parameter B is related to the excess chemical potential $\mu'$ as follows: $B=\mu'/kT+\ln<N>$, where k is Boltzmann's constant, T is the absolute temperature, and <N> is the mean number of molecules of the ORF, which here is $H_2O$. In the method of simulated annealing of chemical potential, the simulation is started with a large initial B-value so that a higher percentage of water insertion attempts are accepted. This causes the simulation cell to be flooded with water molecules. After this grand canonical ensemble simulation at high excess chemical potential is equilibrated, subsequent simulations are carried out at successively lower B-values. This successive lowering of the B-values causes a gradual removal of the bulk water molecules from the simulation cell. As the chemical potential is further "annealed", a point is reached at which water molecules do not readily leave the cell, thereby identifying those water molecules that are strongly influenced by the DNA, the so-called "bound water molecules". As the excess chemical potential is again lowered, ultimately some of these bound waters start to leave the cell. Since chemical potential is a free energy, this simulated annealing of chemical potential yields a numerical estimate of the differential free energy of binding of the different bound water molecules. It must be emphasized that our utilization of the term "annealing" applies strictly to the value of the chemical potential and that the temperature is kept constant at, for example, 298 K in all the simulations. For all simulations the DNA was held fixed, water molecules were added and deleted throughout all parts of the cell, extensive canonical Monte Carlo was performed between accepted grand canonical Monte Carlo steps, and periodic boundary conditions were used.

As an illustration of the method, a simulated annealing of chemical potential on a d(CGCGAATTCGCG)$_2$ was performed, starting with B=1.0 down to −26 in 37 increments performing 2,000,000 cavity-biased grand canonical ensemble Monte Carlo steps at each B-value. The final configuration of the simulation with B=−6, has 1120 bound water molecules. The final configuration of the simulation with B=−8, has 533 bound water molecules. The final configuration of the simulation with B=−9, has 390 bound water molecules. The final configuration of the simulation with B=−11, has 215 bound water molecules. The most salient feature of this progression is the differential hydration of the major and minor groove of the DNA. The B=−6 simulation shows the DNA essentially uniformly solvated. The B=−8 simulation clearly shows that upon lowering of the chemical potential by 2 B-units, a majority of the nonbulk extracted waters come from the major groove, while the minor groove remains almost unaffected. Annealing the chemical potential further (B=−9) still leaves the minor groove well hydrated while the major groove is almost stripped. Lowering B even further (B=−11) results in the removal of almost all water molecules from both the major and minor groove. Quantitation of the hydration of the DNA as a function of chemical potential was computed by proximity analysis (Mehrotra, P. K., and Beveridge, D. L., J. Am. Chem. Soc. 102:4287(1980): Mezei, M., Mol. Simul. 1:327–332 (1988) (describing the effects of different partial charges on proximity analysis)) with the results shown in Table 1:

| | first hydration shell | | | | first and second hydration shell | | | |
|---|---|---|---|---|---|---|---|---|
| | minor groove | | major groove | | minor groove | | major groove | |
| B | no. of waters | density | no. of waters | density | no. of waters | density | no. of waters | density |
| −6 | 7.27 | 0.013 | 13.23 | 0.012 | 21.3 | 0.021 | 41.7 | 0.011 |
| −8 | 5.4 | 0.010 | 5.06 | 0.004 | 14.6 | 0.015 | 11.8 | 0.003 |
| −9 | 4.08 | 0.007 | 4.36 | 0.004 | 11.5 | 0.011 | 9.7 | 0.003 |
| −11 | 1.04 | 0.002 | 2.11 | 0.002 | 3.9 | 0.004 | 4.2 | 0.001 |

For B=−6, the first hydration shell (defined by the position of the first minimum of the radial distribution function) of the major and minor groove has a comparable density (0.012 and 0.013, respectively), while the second hydration shell of the minor groove has twice the density of the major groove. For B=−8 the hydration difference becomes quite pronounced with the minor groove first and second shell hydration density being 2.5 fold and fold higher than the major groove, respectively. For B=−11 the major and minor groove hydration density again becomes equal because at this value of the excess chemical potential both grooves are essentially stripped bare.

Illustrating the differential hydration propensities of the major and minor grooves of DNA is computationally undemanding (3 days of CPU time to run one annealing schedule and 3 days of CPU time to run one proximity analysis (Mezei. M., and Beveridge, D. L,. in *Methods in Enzymology*, Packer. ed., Academic Press. New York., pp. 21–47 (1986) (describing the effects of volume element calculations—which can be CPU intensive—on proximity analysis)) on an SGI Power Challenge) using simulated annealing of chemical potential because only a coarse "cooling" schedule of the chemical potential is required. Since the chemical potential is a free energy, a very fine cooling schedule maybe used to estimate quantitatively the hydration free energy difference of two different functional groups or even two different atoms of the DNA: Two atoms that desolvate at the same B-value have similar solvation free energy, or alternatively, require a finer cooling schedule to resolve the differences. It should be noted that the model system used here consisted of ionic DNA with 22 negative charges and no sodium counterions. The findings presented herein about the preferential hydration of the minor groove corresponds very well to results from X-ray crystallographic and NMR studies. Possible reasons for the stronger binding of water molecules in the minor groove may include the following: the high density of the charged rows of phosphate groups, steric constraints, and specific water—water, water—DNA interactions.

The regions where water binds tightly on a protein, are regions which are precluded from ORF binding. Thus, the remaining sites on the protein unoccupied by water are candidates for good ORF binding.

Antagonists and Agonists—Assays and Molecules

Candidate bioactive agents identified by the methods of the invention can be tested to assess their binding to the macromolecule in question. Where the macromolecules are responsible for many biological functions, including disease states, it is therefore desirable to devise screening methods to identify compounds which stimulate or which inhibit the function of the macromolecule. Accordingly, in a further aspect, the present invention provides for a method of screening compounds to identify those which stimulate or which inhibit the function of such a macromolecule. In general, agonists or antagonists can be employed for therapeutic and prophylactic purposes for diseases. Compounds can be identified from a variety of sources, for example, cells, cell-free preparations, chemical libraries, and natural product mixtures.

The screening methods can simply measure the binding of a candidate compound to the macromolecule, or to cells or membranes bearing the macromolecule. The macromolecule can be a variant of the macromolecule used in the simulation method, such as a fragment retaining the binding site identified in the simulation or a fusion protein used to make recombinant synthetic methods more practical. The screening method can involve competition with a labeled competitor. Further, these screening methods can test whether the candidate compound results in a signal generated by activation or inhibition of the macromolecule, using detection systems appropriate to the cells comprising the macromolecule. Inhibitors of activation are generally assayed in the presence of a known agonist and the effect on activation by the agonist by the presence of the candidate compound is observed. Further, the screening methods can simply comprise the steps of mixing a candidate compound with a solution containing a macromolecule, measuring macromolecule activity in the mixture, and comparing the activity of the mixture to a standard.

The invention also provides a method of screening compounds to identify those which enhance (agonist) or block (antagonist) the action of macromolecules, including association of the macromolecule with itself or another macromolecule. The method of screening can involve high-throughput techniques. For example, to screen for agonists or antagonists, a synthetic reaction mix, a cellular compartment, such as a membrane, cell envelope or cell wall, or a preparation of any thereof, comprising macromolecule and a labeled substrate or ligand of such polypeptide is incubated in the absence or the presence of a candidate molecule that can be a agonist or antagonist. The ability of the candidate molecule to agonize or antagonize the macromolecule is reflected in decreased binding of the labeled ligand or decreased production of product from a substrate. Molecules that bind gratuitously, i.e., without inducing the effects of macromolecule are most likely to be good antagonists. Molecules that bind well and, as the case can be, increase for example the rate of product production from substrate, increase signal transduction, or increase chemical channel activity are agonists. Detection of the rate or level of, as the case can be, production of product from substrate, signal transduction, or chemical channel activity can be enhanced by using a reporter system. Reporter systems that can be useful in this regard include but are not limited to calorimetric, labeled substrate converted into product, a reporter gene that is responsive to changes in macromolecule activity, and binding assays known in the art.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A computer-implemented method of analyzing a macromolecule for potential binding sites, comprising:

(1) positioning an instance of a computer represculation of a molecule or molecular fragment at a plurality of sampling sites of the macromolecule;

(2) selecting a value of B, wherein $R=\mu'/kT+1n<N>$, where $\mu'$ the excess chemical potential, k is Boltzmann's constant, T is the absolute temperature, and $<N>$ is the mean number of molecules of the molecule or molecular fragment;

(3) repositioning the instances of the molecule or molecular fragment;

(4) accepting or rejecting each instance of the repositioned molecule or molecular fragment based on the Metropolis sampling criteria using the computer binding energy compared to the selected value of B;

(5) repeating steps (1) through (4) at a lesser value of B;

(6) outputting a list of unrejected instances of the molecule or molecular fragment, wherein the molecule or molecular fragment of steps (1)–(6) is organic fragment; and (7) outputting a list of one or more clusters of sampling sites, wherein the clusters of sampling sites comprise closely located or superimposed sampling sites associated with the unrejected instances of the molecule or molecular fragment outputted step (6).

2. The method according to claim 1, further comprising:

(8) repeating steps (1) through (6) for one or more additional molecules or molecular fragments, wherein said molecules or molecular fragments are organic fragments, wherein steps (7) comprises outputting a list of one or more clusters of sampling sites, wherein the clusters of sampling sites comprise closely located or superimposed sampling sites associated with unrejected instances of two or more distinct molecules or molecular fragments outputted in steps (6) and (8).

3. The method of recording to claim 2, wherein a the clusters of sampling sites comprise closely located or superimposed sampling sites associated with unrejected instances of three or more distinct molecules or molecular fragment outputted in steps (6) and (8).

4. The method according to claim 2, further comprising:

(9) selecting a value B', wherein B' is a value higher than the lower value of B at which steps (1) through (4) were performed,

(10) repeating steps (1) through (5) for one or more molecules or molecular fragments, wherein the value of B selected in step (2) is greater than or equal to B'; and

(11) outputting a list of unrejected instances of the molecules or molecular fragments that are in the vicinity of a cluster of sampling sites outputted in step (7).

5. The method according to claim 1, wherein said molecule or molecular fragment is selected from the group consisting of acetone, aldehyde, amide, ammonia, benzeue, carboxilic acid, 1,4-diazine, ester, ether, formadehyde, furan, imidazole, methane, methanol, phospho-acid, pyridine, pyrimidine, pyrrole, thiol and thiophene.

6. The method according to clam 1, wherein step (3) comprises using a forced bias canonical probability density function.

7. The method according to claim 1, wherein step (4) comprises using a grand canonical ensemble probability density function.

8. A computer-implemented method of analyzing a macromolecule for potential binding sites, further comprising:

(1) positioning an instance of a computer representation of a molecule or molecular fragment at a plurality of sampling sites of the macromolecule;

(2) selecting a value of B, wherein $B=\mu'/kT+1n <N>$, wherein $\mu'$ the excess chemical potential, k is Boltzmann's constant T is the absolute temperature; and $<N>$ is the mean number of molecules of the molecule or molecular fragment;

(3) repositioning the instances of the molecule or molecular fragment;

(4) accepting or rejecting each instance of the repositioned molecule or molecular fragment based on the Metropolis sampling criteria using the computed binding energy compared to the selected value of B;

(5) repeating steps (1) through (4) at a leaser value of B; wherein the molecule molecular fragment of steps (1)–(5) is an organic fragment;

(6) outputting a list of unrejected instances of the molecule or molecular fragment;

(7) repeating steps (1) through (5) wherein the molecule or molecular fragment is a water molecule, and outputting a list of the unrejected instances of the molecule or molecular fragment of step (6) that are not associated with unrejected instances of the water molecule; and (8) outputting a list of one or more clusters of sampling sites, wherein the clusters of sampling sites comprise closely located or superimposed sampling sites associated with the unrejected instances of the molecule or molecular fragment outputted in step (7).

9. The method according to claim 8, further comprising:

(9) repeating steps (1) through (6) for one or more additional molecules or molecular fragments, wherein said molecules or molecular fragments are organic fragments, wherein step (7) comprises repeating steps (1) through (5) wherein the molecule or molecular fragment is a water molecule, and outputting a list of the unrejected instances of the molecule or molecular fragment of steps (6) and (9) that are not associated with unrejected instances of the water molecule.

10. The method according to claim 9, further comprising:

(10) selecting a value B', wherein B' is a value higher than the lowest value of B at which steps (1) through (4) were performed;

(11) repeating steps (1) through (5) for one or more molecules or molecular fragments, wherein the value of B selected in step (2) is greater than or equal to B'; and

(12) outputting a list unrejected instances of the molecules or molecular fragments that are in the vicinity of a cluster of sampling sites outputted in step (8).

* * * * *

UNITED STATES PATENT AND TRADEMARK OFFICE
CERTIFICATE OF CORRECTION

PATENT NO. : 6,735,530 B1
DATED : May 11, 2004
INVENTOR(S) : Frank Guarnieri

It is certified that error appears in the above-identified patent and that said Letters Patent is hereby corrected as shown below:

Title page,
Item [56], References Cited, OTHER PUBLICATIONS, please insert the following:
-- Mezei, M., and Beveridge, D.L., "Structural Chemistry of Bimolecular Hydration via Computer Simulation: The Proximity Criterion," in *Methods in Enzymology*, Parker, ed., Academic Press, NY, pp. 21-47(1986).
Mezei, M., "Modified Proximity Criteria for the Analysis of the Solvation of a Polyfunctional Solute," *Mol. Simul. 1*:327-332, Gordon and Breach Science Publishers S.A. (1988).
Mezei, M., "Grand-canonical ensemble Monte Carlo study of dense liquid Lennard-Jones, soft spheres and water," *Mol. Phys. 61*:565-582, Taylor and Francis (1994).
Mehrotra, P.K., and Beveridge, D.L., "Structural Analysis of Molecular Solutions Based on Quasi-Component Distribution Functions," *J. Am. Chem. Soc. 102*:4287, American Chemical Society (1980).
Metropolis, N., *et al.*, "Equation of State Calculations by Fast Computing Machines," *J. Chem. Phys. 21*:1087-1092, American Institute of Physics (1953).
Resat, H., and Mezei, M., "Grand canonical Monte Carlo Simulation of Water Positions in Crystal Hydrates," *J. Am. Chem. Soc. 116*:7451-7452, American Chemical Society (1994).--.

Column 3,
Line 55, please replace "Boactive" with -- Bioactive --.

Column 4,
Line 47, please replace ""ORFs" with -- "ORFs" --.

Column 8,
Line 19, please replace "prolyl-pisopropylanilide" with -- prolyl-*p*-isopropylanilide --.

Column 9,
Line 13, please replace "*Strict.*" with -- *Struct.* --.
Line 19, please replace "n-tert-butoxycarbonyl" with -- n-(tert-butoxycarbonyl --.

Column 10,
Line 46 (equation 5), please replace "+1N>" with -- +1n<N> --.
Line 66, please replace "IIV" with -- 1/V --.

Column 11,
Line 32 (equation 8), please replace "$P_N^{cav}N$" with -- $P_N^{cav}V$ --.
Line 38, please replace "$P_N^{cav}N$" with -- $P_N^{cav}V$ --.

Column 13,
Line 23, please replace "and fold" with -- and 5 fold --.
Line 42, please replace "DNA:" with -- DNA. --.

UNITED STATES PATENT AND TRADEMARK OFFICE
CERTIFICATE OF CORRECTION

PATENT NO. : 6,735,530 B1
DATED : May 11, 2004
INVENTOR(S) : Frank Guarnieri

It is certified that error appears in the above-identified patent and that said Letters Patent is hereby corrected as shown below:

Column 14,
Line 54, please replace "calorimetric" with -- colorimetric --.

Column 15,
Line 10, please replace "represculation" with -- representation --.
Line 13, please replace "R=" with -- B= --.
Line 14, please replace "$\mu$' the" with -- $\mu$' is the --.
Line 29, please replace "is organic" with -- is an organic --.
Line 34, please replace "outputted step" with -- outputted in step --.
Line 40, please replace "steps" with -- step --.
Line 46, please replace "of recording" with -- according --.
Line 46, please delete the "a" after "wherein".
Line 50, please replace "fragment" with -- fragments --.
Line 53, please replace "lower" with -- lowest --.
Line 54, please replace "performed," with -- performed; --.
Line 63, please replace "benzeue" with -- benzene --.
Line 64, please replace "formadehyde" with -- formaldehyde --.

Column 16,
Line 10, please delete "further".
Line 16, please replace "$\mu$." the" with -- $\mu$' is the --.
Line 17, please replace "constant T" with -- constant, T --.
Line 17, please replace "temperature;" with -- temperature," --.
Line 27, please replace "leaser" with -- lesser --.
Line 28, please replace "molecule molecular" with -- molecule or molecular --.
Line 60, please replace "list unrejected" with -- list of unrejected --.

Signed and Sealed this

Eighth Day of February, 2005

JON W. DUDAS
*Director of the United States Patent and Trademark Office*